(12) United States Patent
Cherpeck et al.

(10) Patent No.: US 8,920,524 B2
(45) Date of Patent: *Dec. 30, 2014

(54) POLYISOBUTENYL ALCOHOLS AND FUEL COMPOSITIONS

(75) Inventors: Richard E. Cherpeck, Cotati, CA (US); Ruth Smocha, San Francisco, CA (US)

(73) Assignee: Chevron Oronite Company LLC, San Ramon, CA (US)

( * ) Notice: Subject to any disclaimer, the term of this patent is extended or adjusted under 35 U.S.C. 154(b) by 565 days.

This patent is subject to a terminal disclaimer.

(21) Appl. No.: 12/968,615

(22) Filed: Dec. 15, 2010

(65) Prior Publication Data

US 2012/0151830 A1    Jun. 21, 2012

Related U.S. Application Data

(60) Provisional application No. 61/288,096, filed on Dec. 18, 2009.

(51) Int. Cl.
*C10L 1/182* (2006.01)
*C10L 1/19* (2006.01)

(52) U.S. Cl.
USPC ............ 44/400; 44/413; 44/414; 44/451; 44/384; 560/64; 560/183; 568/700; 568/715

(58) Field of Classification Search
USPC ............ 44/384, 400, 412, 414; 508/542; 568/705, 909.5
See application file for complete search history.

(56) References Cited

U.S. PATENT DOCUMENTS

| | | | |
|---|---|---|---|
| 4,163,730 A | 8/1979 | Bryant | |
| 4,832,702 A | 5/1989 | Kummer et al. | |
| 4,859,201 A | 8/1989 | Marsh | |
| 4,859,210 A | 8/1989 | Franz et al. | |
| 5,055,607 A | 10/1991 | Buckley, III | |
| 5,300,701 A | 4/1994 | Cherpeck | |
| 5,399,178 A | 3/1995 | Cherpeck | |
| 5,413,615 A | 5/1995 | Cherpeck | |
| 5,559,191 A | 9/1996 | Blackborow | |
| 5,827,344 A | 10/1998 | Fyles et al. | |
| 5,873,917 A | 2/1999 | Daly | |
| 6,039,733 A | 3/2000 | Buysse et al. | |
| 6,262,310 B1 | 7/2001 | Dever et al. | |
| 6,533,830 B1 | 3/2003 | Oppenlander et al. | |
| 7,291,681 B2 | 11/2007 | Rath et al. | |
| 7,435,273 B2 | 10/2008 | Lange et al. | |
| 7,498,386 B2 | 3/2009 | Karl et al. | |
| 2004/0260032 A1 | 12/2004 | Irving et al. | |
| 2008/0027187 A1 | 1/2008 | Rausa | |
| 2008/0242790 A1 | 10/2008 | Leyrer et al. | |
| 2008/0274924 A1 * | 11/2008 | Lange et al. | 508/542 |
| 2009/0216025 A1 | 8/2009 | Jamison et al. | |

FOREIGN PATENT DOCUMENTS

| | | | |
|---|---|---|---|
| JP | 2000169407 | | 6/2000 |
| JP | 2000169407 A | * | 6/2000 |
| WO | WO2007027752 | | 8/2007 |

OTHER PUBLICATIONS

English Translation of JP 2000-169407A.*
Biermann, Ursula and Metzger J.O., "Lewis Acid Catalyzed Additions to Unsaturated Fatty Compounds* II: Alkylaluminium Halide Catalyzed Ene Reactions of Unsaturated Fatty Compounds and Formaldehyde**'". Fat Sci. Technol. 93. Jahrgang Nr. 8 1991, pp. 282-284.
Snider, Barry B., Rodini, David J., Kirk, Thomas, C., and Cordova, Robert, "Dimethylaluminum Chloride Catalyzed Ene Reactions of Aldehydes", J. Am. Chem. Soc., 1982, 104, pp. 555-563.
Mikami, Koichi, and Shimizu, Masaki., "Asymmetric Ene Reactions in Organic Synthesis". Chem. Rev. , 1992, 92, pp. 1021-1050.
Behr, Arno, and Fiene, Martin., "Lewis-acid catalysed ene reaction of electrondeficient aldehydes and ketones at unsaturated fatty acid derivatives". Eur. J. Lipid Sci. Technol. 2000, 212-217.
Hoffmann, H.M.R., "The Ene Reaction". Angew. Chem. Internet. Edit., vol. 8, 1969, No. 8, pp. 556-577.
Huston, Gerri E., Dave, Apurva H., and Rawal, Viresh H., "Highly Enantioselective Carbonyl-ene Reactions Catalyzed by a Hindered Silyl-Salen-Cobalt Complex". Organic Letters, 2007, vol. 9, No. 20, pp. 3869-3872.
Jackson, Andrew C., Goldman, Boris, E., and Snider, Barry B., "Intramolecular and Intermolecular Lewis Acid Catalyzed Ene Reactions Using Ketones as Enophiles", J. Org. Chem., 1984, vol. 49, pp. 3988-3994.
Snider, Barry, B., "Lewis-Acid-Catalyzed Ene Reactions"., Acc. Chem. Res. 1980, 13, pp. 426-432.
PCT Search Report and the Written Opinion of the International Searching Authority, PCT/US2010/060549, Sep. 1, 2011.

* cited by examiner

Primary Examiner — Ellen McAvoy
Assistant Examiner — Latosha Hines
(74) Attorney, Agent, or Firm — Joseph P. Foley

(57) ABSTRACT

Disclosed are polyisobutenyl alcohols and substituted polyisobuentyl alcohols of the formula:

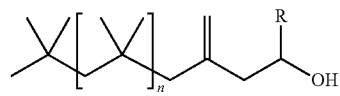

wherein n is an integer from 5 to 90, R is selected from the group consisting of hydrogen, haloalkyl, alkoxycarbonyl and substituted aryl wherein at least one substituent group of the substituted aryl is selected from cyano, nitro and alkoxycarbonyl.

13 Claims, No Drawings

POLYISOBUTENYL ALCOHOLS AND FUEL COMPOSITIONS

CROSS REFERENCE TO RELATED APPLICATION

This application claims the benefit of U.S. Provisional Application 61/288,096 filed Dec. 18, 2009.

FIELD OF THE INVENTION

The present invention is directed to polyisobutenyl alcohols and more particularly to substituted hydroxymethylpolyisobutylene compounds prepared via the carbonyl-ene reaction. Such compounds are useful carrier fluids for fuel additives and in fuel compositions.

BACKGROUND OF THE INVENTION

Alcohols derived from polyalkanes, and more specifically, polyisobutyl alcohols have been used as carrier fluids for fuel additives and employed in fuel compositions; largely since they are relatively inexpensive to prepare, can be prepared halogen free, compatible with other additives typically employed, and by themselves may contribute some detergent action. Carrier fluids are commonly employed with fuel additives and they may serve several functions such as improving viscometrics/compatibility/mobility of the fuel additives or active ingredients and may assist in the desired functionality of the additive. Additionally, polyisobutyl alcohols have served as a precursor for the preparation of fuel additives for controlling engine deposits, as described in U.S. Pat. Nos. 5,055,607; 5,399,178; 5,413,615; 5,827,344; 6,039,733 and 4,859,210.

Typically these polyisobutyl alcohols have been prepared from polyisobutylene via hydroformulation at high temperature and high pressures (U.S. Pat. Nos. 3,429,936; 4,859,210) or via hydroboration of polyisobutene followed by oxidation (U.S. Pat. No. 5,055,607). The efficiency of the hydroformylation reaction as applied to polyisobutylene varies with the type of polymer, and conversions range from 59-81% employing the most reactive polyisobutenes (see U.S. Pat. No. 4,832,702). The polyisobutyl alcohols of the prior art are saturated compounds requiring expensive processing equipment due to the elevated temperature and pressures.

The present invention is directed to novel polyisobutenyl alcohols and substituted polyisobutenyl alcohols by reaction pathway not known or appreciated in the art. The present invention employs moderate temperatures and pressures and can lead to product in high yield. The functionalization of polyisobutene via the carbonyl-ene reaction leads to these new compounds which are suitable for use as carrier fluids and additives in fuel applications.

SUMMARY OF THE INVENTION

An aspect of the present invention is directed to polyisobutenyl alcohols and substituted polyisobutenyl alcohols, and to fuel additive compositions containing them. The polyisobutenyl alcohols and substituted polyisobutenyl alcohols are suitable as carrier fluids for fuel additives, which are also referred to as fuel detergents. Additionally, it is thought that some of these polyisobutenyl alcohols and substituted alcohols may improve or impart detergency/dispersancy by themselves or act synergistically with other fuel additives.

Accordingly, disclosed is a compound of the formula I:

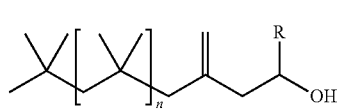

Formula I wherein n is an integer from 5 to 90, R is selected from the group consisting of hydrogen, haloalkyl, alkoxycarbonyl and substituted aryl wherein at least one substituent group of the substituted aryl is selected from cyano, nitro and alkoxycarbonyl. The substituted aryl may be optionally substituted with from 1 to 3 substituents selected from alkyl from 1 to 6 carbon atoms, alkoxy, cycloalkyl, and alkaryl. In one aspect n is an integer from 6 to 52 and more preferably n is an integer from 14 to 42.

An aspect of the compound of Formula I is directed to wherein R is selected from hydrogen, alkoxycarbonyl and a mono substituted aryl. Thus, in one aspect R can be hydrogen. In another aspect R is an alkoxycarbonyl group of the formula —C(O)OR$_2$ wherein R$_2$ is alkyl from 1 to 6 carbon atoms. In this respect, the compounds can be described as polyisobutene α-hydroxy esters and may be illustrated by formula Ia

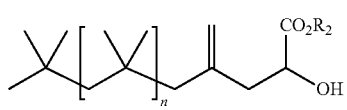

Formula Ia wherein n is an integer for 5 to 90 and R$_2$ is alkyl from 1 to 6 carbons. In one aspect n is an integer from 6 to 52 and more preferably n is an integer from 14 to 42. In an aspect, R$_2$ is methyl, ethyl, propyl, isopropyl, butyl, isobutyl, sec-butyl, t-butyl, and pentyl. More particularly R$_2$ is methyl, ethyl or isopropyl.

Another aspect is directed to where R is a substituted aryl group. Another embodiment is directed to the compound of formula II

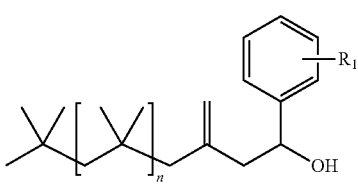

Formula II wherein R$_1$ is selected from the group consisting of cyano, nitro and —C(O)OR$_2$ wherein R$_2$ is alkyl from 1 to 6 carbon atoms. In one aspect n is an integer from 5 to 90; preferably, n is an integer from 6 to 52; and more preferably, n is an integer from 14 to 42. In a preferred aspect, R$_1$ is in the para position. In one aspect, nitro and cyano groups are selected. In another aspect R$_1$ is —C(O)OR$_2$ wherein R$_2$ is alkyl from 1 to 6 carbon atoms.

The polyisobutenyl alcohols and substituted polyisobutenyl alcohols are suitable for use as additives and/or carrier fluids in hydrocarbons fuels applications. Accordingly one aspect is directed to a fuel composition comprising a major amount of hydrocarbons boiling in the gasoline or diesel range;

a. 100 to 5000 ppm of the compound:

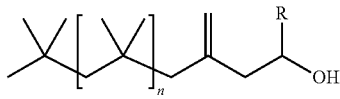

wherein n is an integer from 5 to 90, R is selected from the group consisting of hydrogen, alkoxycarbonyl and substituted aryl wherein at least one substituent group of the substituted aryl is selected from cyano, nitro and alkoxycarbonyl; and b. 50 to 2500 ppm of a nitrogen containing detergent.

In the fuel composition above, particularly preferred nitrogen containing detergents are selected from the group consisting of aliphatic hydrocarbyl amines, hydrocarbyl-substituted poly(oxyalkylene)amines, hydrocarbyl-substituted succinimides, Mannich reaction products, nitro and amino aromatic esters of polyalkylphenoxyalkanols, polyalkylphenoxyaminoalkanes, and mixtures thereof.

DETAILED DESCRIPTION OF THE INVENTION

As used herein, the terms used have the following meaning:

As used herein, unless otherwise specified the term "alkyl" means a straight chain or branched saturated hydrocarbon moiety. "Lower alkyl" means an alkyl group having 1 to 6 carbon atoms.

As used herein, unless otherwise specified the term "halogen" means fluorine, chlorine, bromine, or iodine.

As used herein, unless otherwise specified the term "haloalkyl" refers to an alkyl radical, as defined above, that is substituted by one or more halogen radicals, as defined above, e.g., trifluoromethyl, difluoromethyl, trichloromethyl, 2,2,2-trifluoroethyl, 1-fluoromethyl-2-fluoroethyl, 3-bromo-2-fluoropropyl, 1-bromomethyl-2-bromoethyl, and the like.

As used herein, unless otherwise specified the term "acyl" means —C(O)R* where R* is hydrogen, alkyl or aryl defined herein. The term "lower acyl" refers to where R* is a lower alkyl defined above.

As used herein, unless otherwise specified the term "carboxyl" means —COOH.

As used herein, unless otherwise specified the term "alkoxy" means —O-(alkyl), wherein alkyl is defined above.

As used herein, unless otherwise specified the term "alkoxycarbonyl" means —C(=O)O-(alkyl), wherein alkyl is defined above.

As used herein, unless otherwise specified the term "alkoxy alkyl" means -(alkyl)-O-(alkyl), wherein each "alkyl" is independently an alkyl group as defined above.

As used herein, unless otherwise specified the term "aryl" means a carbocyclic aromatic ring containing from 5 to 14 ring atoms. The ring atoms of a carbocyclic aryl group are all carbon atoms, such as, phenyl, tolyl, fluorenyl, indenyl, azulenyl, and naphthyl, as well as benzo-fused carbocyclic moieties such as 5,6,7,8-tetrahydronaphthyl and the like. A carbocyclic aryl group can be unsubstituted or substituted by 1 to 3 substituents selected from halogen, carboxyl, acyl, lower acyl, carboxyl, alkoxycarbonyl, cyano and nitro.

As used herein, unless otherwise specified the term "aryloxy" means —O-aryl group, wherein aryl is as defined above. An aryloxy group can be unsubstituted or substituted.

As used herein, unless otherwise specified the term "arylalkyl" means -(alkyl)-(aryl), wherein alkyl and aryl are defined above.

As used herein, unless otherwise specified the term "arylalkyloxy" means —O-(alkyl)-(aryl), wherein alkyl and aryl are defined above.

As used herein, unless otherwise specified the term "cycloalkyl" means a monocyclic or polycyclic saturated ring comprising carbon and hydrogen atoms and having no carbon-carbon multiple bonds. A cycloalkyl group can be unsubstituted or substituted. Preferably, the cycloalkyl group is a monocyclic ring or bicyclic ring.

As used herein, unless otherwise specified the term "catalytic amount" is recognized in the art and means a sub-stoichiometric amount relative to the reactant.

As used herein, unless otherwise specified the term "electron withdrawing group" means a functionality which draws electrons to itself more than a hydrogen atom would at the same position. Exemplary electron withdrawing groups include carbonyl groups, halogen groups, nitro groups, cyano groups and the like.

Polyisobutenes

The polyisobutenes employed in the present invention are characterized by having a large percentage of terminal double bonds and for purposes of the present invention are referred to as reactive polyisobutene or highly reactive polyisobutene. This is in contrast to "conventional" polyisobutylene which has nonreactive chain end such as —C(CH$_3$)=C(CH$_3$)—CH (CH$_3$)$_2$ which do not readily undergo reaction in the carbonyl-ene reaction scheme. Conventional polyisobutene typically contains approximately 90% or greater of the internal bonds and thus are unsuitable; these internal olefins are not reactive in the scheme of the present invention. Thus, highly reactive polyisobutenes containing a high mole percentage of alkylvinylidene and 1,1-dialkyl isomers such as the methyl vinylidene isomer. Typically the polyisobutenes are mixtures of polyisobutene having 32 to 360 carbon atom. The polyisobutenes mixture comprises greater than 50 mole percent of the reactive methyl vinylidene isomer, preferably greater than 70 mole percent of the reactive methyl vinylidene isomer, more preferably greater than 80 mole percent of the reactive methyl vinylidene isomer.

The polyisobutenes have a number average molecular weight in the range of about 450 to about 5000. Polyisobutenes having number average molecular weights from about 550, 1000, 1300 or 2300, and mixtures thereof, are particularly useful. The polyisobutenes are selected to have a number average molecular weight from 450 to 5,000; a preferred aspect is directed to number average molecular weights from 450 to 3,000; more particularly to a number average molecular weights from 700 to 3,000 and even more preferably having a number average molecular weight from 900 to 2,500.

The reactive polyisobutenes having a high content of olefinically unsaturated terminal groups are known in the art and typically prepared by cationic polymerization of isobutene or isobutene-containing hydrocarbon steams in the presence of boron trifluoride complex catalyses. For example suitable methods are described in U.S. Pat. Nos. 4,152,499; 5,286, 823, 5408,018; EP-A 145 235, EP-A 481 297, EP 671 419, EP-A 628 575, EP-A 807 641, WO 99/31151 and the like.

Enophile

An aspect of the invention comprises the use of a suitable enophile which comprises a carbonyl compound or carbonyl precursor. More particularly, preferred enophiles are selected from reactive i.e. electron deficient, aldehyde, where reactivity may be effected by steric and electronic effects of the enophile or by strained enophiles such as where the reaction results in the relief of steric congestion. Preferred enophiles may be described as reactive aldehydes having the structure,

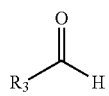

wherein $R_3$ can be hydrogen, haloalkyl, alkoxycarbonyl and aryl substituted with at least one electron withdrawing group selected from nitro, cyano, and alkoxycarbonyl.

Preferably the carbonyl compound or carbonyl precursor is an aldehyde or paraformaldehyde. A suitable aldehyde is formaldehyde which may also be in the polymerized form paraformaldehyde or trioxane. When formaldehyde is used as the enophile with a highly reactive polyisobutene as the ene, under reactive conditions with a suitable Lewis acid; the compound prepared is a ω-hydroxymethyl polyisobutene compound.

In the case where $R_3$ is hydrogen, the aldehyde is formaldehyde. By formaldehyde it is meant in all its forms including gaseous, liquid and a solid and formaldehyde equivalents. Formaldehyde equivalents include but are not limited to paraformaldehyde, (polymerized formaldehyde $(CH_2O)_n$) or 1,3,5-trioxane (the cyclic trimer of formaldehyde). Formaldehyde solutions are commercially available in water and various alcohols, e.g. formalin is a 37% solution in water. Clearly aqueous solutions are is not suitable with moisture sensitive Lewis acids. Paraformaldehyde is a solid typically a powder or flaked product containing the equivalent of about 91% to 93% formaldehyde. Aqueous formalin solutions are undesirable due to the negative effects exercised by their water fraction.

Formaldehyde is generally more reactive relative to other substituted aldehydes, in that the carbon of formaldehyde is relatively more electrophilic. That is, substitution at the carbonyl by, for example, an alkyl or aryl group may stabilize the carbonyl, making it relatively less reactive than formaldehyde. However, electron withdrawing groups strategically placed on the substituent group can improve the carbonyl reactivity and lead to suitable substituted aldehydes.

Thus for example, chloral and other haloalkyl substituted aldehydes are suitably reactive to adduct with the polyisobutene in the presence of a suitable Lewis acid. Halogen substituents however, are not particularly well suited for commercial engine applications.

In a particularly preferred aldehyde, $R_3$ above is selected from an alkoxycarbonyl substituted having an alkyl group from 1 to 6 carbon atoms. These compounds can also be referred to as glyoxylate compounds of the formula:

wherein $R_4$ is alkyl from 1 to 6 carbon atoms and mixtures thereof. Preferred compounds include methyl glyoxylate, ethyl glyoxylate, isopropyl glyoxylate, n-butyl glyoxylate, and t-butyl glyoxylate. Particularly preferred is methyl glyoxylate.

Another aspect is directed to where $R_3$ is an aryl substituted with at least one electron withdrawing group selected from nitro, cyano, and alkoxycarbonyl wherein the alkyl group is from 1 to 6 carbon atoms. The aryl group may optionally be substituted with 1 to 3 substituents which do not impart significant steric hindrance or significantly negate the impact of the electron withdrawing group. In this aspect, when the aryl group is benzene, the electron withdrawing group is preferably positioned para to the carbonyl group. Thus particularly preferred compounds are substituted benzaldehydes, more preferably selected from 4-nitro benzaldehyde, 4 cyano benzaldehyde and 4-$C_{1-6}$ alkyl esters of benzaldehyde.

Screening tests may be employed to determine which aldehydes in combination with Lewis acids may be preferred for use in the present invention, including subjecting an aldehyde to the reaction conditions described herein. The carbonyl ene reaction described herein, can easily be carried out and require relatively short reaction times, allowing a wide ranges of aldehydes and Lewis acid pairs to be tested and reaction conditions optimized.

The molar ratio of polyisobutene to aldehyde compound may be 1:1 however an excess of polyisobutene moiety relative to the aldehyde compound improves the yields of mono adducted product from the reactions. For example ratios of between 1:1 and 10:1 and preferably 1:1 to 6:1 may be used in the present process.

Lewis Acid

Appropriate Lewis acids and reaction conditions must be chosen so that the carbonyl ene reaction is accelerated in preference to isomerization of the methylvinylidene to less reactive trisubstituted olefins (Scheme 1).

Scheme 1. Lewis Acid Catalyzed Olefin Isomerization

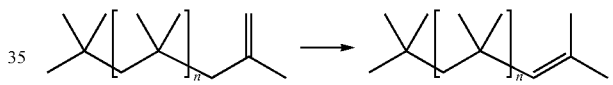

The Lewis acid and reaction conditions must also be chosen so that depolymerization of polyisiobutene (Scheme 2) does not occur.

Scheme 2. Lewis Acid Catalyzed Depolymerization of Polyisobutene

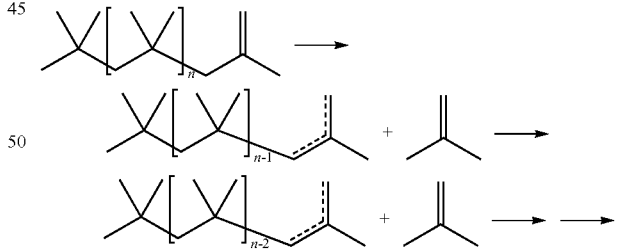

Certain Lewis acids that accomplish this can be used in a catalytic manner, others need to be used stoichiometrically. Lewis acids that can be used in a catalytic manner such as boron trifluoride or boron trifluoride complexes such as boron trifluoride etherate give both mono and bis addition of the carbonyl compound to the polyisobutene because the addition product is also an olefin. A rationalization of this is illustrated in Scheme 3 employing boron trifluoride as the Lewis acid. Mono addition products can be maximized by employing an excess of polyisobutene relative to the carbonyl compound.

Scheme 3. Carbonyl Ene Reaction - Catalytic Lewis Acids
Mono and Bis Products
Boron Trifluoride Example

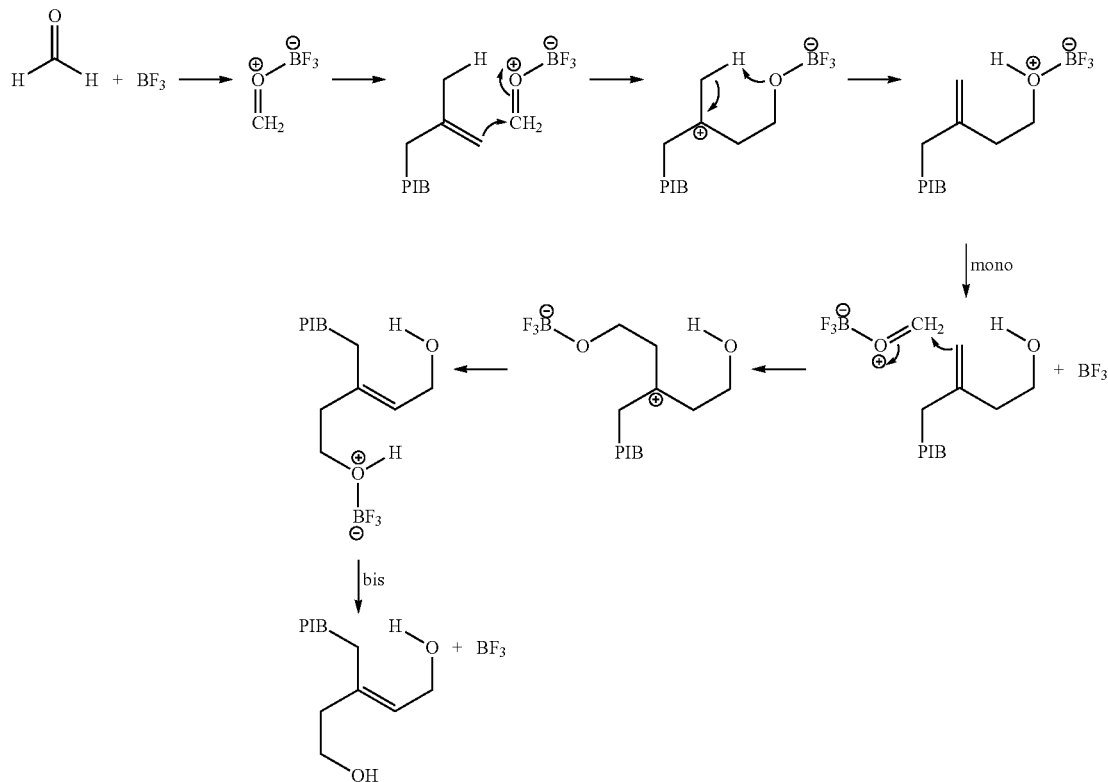

For the catalytic Lewis acids which are not consumed in the carbonyl-ene reaction; the Lewis acid is employed in catalytic quantities to produce the mono adducted polyisobutene alcohols. In general, the number of equivalents of Lewis acid per equivalent of polyisobutene will be in the range of about 0.005:1, and preferably in the range of about 0.005:0.5.

B. Snider, *Acc. Chem. Res.* 1980, 13, 426-432 (1980), has discovered that dimethylaluminum chloride and ethylaluminum dichloride Lewis acids when employed in a stoichiometric amounts give mono addition product of the carbonyl compound to olefins that are not polymeric and not subject to the side reactions that polyisobutene is susceptible to. A rationalization for this employing dimethylaluminum chloride as the Lewis acid is depicted in Scheme 4.

Scheme 4. Carbonyl Ene Reaction - Stoichiometric Lewis Acids
Mono Products
Dimethylaluminum Chloride Example

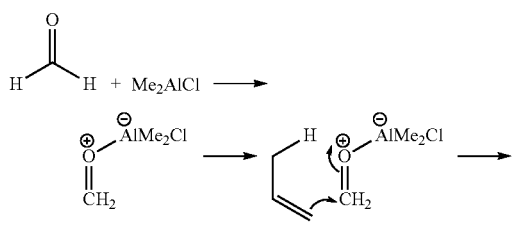

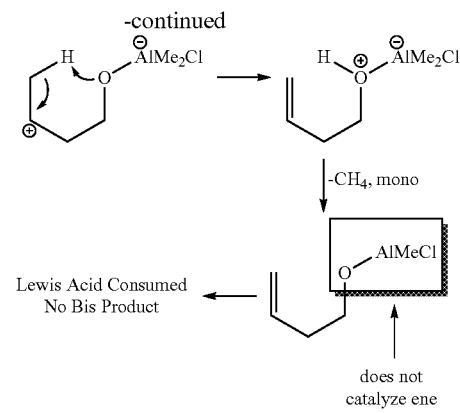

We have discovered that certain Lewis acids when used in stoichiometic quantities can give mono addition products to polyisobutene without degrading the polymer or isomerizing the olefin to the less reactive isomers. Preferred Lewis acids that can do this are alkyl-aluminum halides represented by the formula $R'_y AlX_{(3-y)}$ where R' is a $C_{1-6}$ alkyl; X is halogen: and y is an integer from 1 to 2. Particularly preferred alkyl groups are methyl and ethyl. The preferred halogen is chlorine. Particularly suited Lewis acids are $Me_2AlCl$, $EtAlCl_2$ and similar Lewis acids which do not form side reactions after the primary carbonyl ene reaction.

We have also discovered that another useful Lewis acid to give mono addition products when used stoichiometrically in the carbonyl-ene reaction is a hydrocarbylsilyl halide of the formula: $R''_zSiX_{4-z}$, wherein $R''_z$ is alkyl $C_{1-6}$, aryl, X is halogen, z is an integer from one to two. These hydrocarbylsilyl halides have not previously been used to catalyze the carbonyl-ene reaction. They offer advantages in not being pyrophoric and in their ease of handling.

In general for Lewis acids employed in stoichiometric amounts, the number of equivalents of Lewis acid per equivalent of polyisobutene will be in the range of about 1:10, and preferably in the range of about 1.1:2.0.

Solvent

Solvents are preferably used in the process of the present invention. The solvents are non-polar, with relatively low dielectric constants, which are selected so they do not complex preferentially to the Lewis acid. Suitable solvents include halogenated alkanes such as chloroform, ethylchloride, n-butyl chloride, methylene chloride, methyl chloride, 1,2-dichloroethane, 1,1,2,2-tetrachloroethane, carbon tetrachloride, 1,1-dichloroethane, n-propyl chloride, iso-propyl chloride, 1,2-dichloropropane, or 1,3-dichloropropane, alkenes and halogenated alkenes (such as vinyl chloride, 1,1-dichloroethene, and 1,2-dichloroethene). Suitable solvents can include esters, such as ethyl acetate. Hydrocarbyl solvents may also be employed: such alkanes including normal alkanes such as propane, normal butane, normal pentane, normal hexane, normal heptane, normal octane, normal nonane and normal decane, and branched alkanes including isobutane, isopentane, neopentane, isohexane, 3-methylpentane, 2,2-dimethylbutane, 2,3-dimethylbutane and the like); aromatic solvents such as benzene, toluene, xylene, as the like, including halo substituted aromatic compounds such as chlorobenzene. Solvents may also include mixtures of the above and other known organic compounds used in Lewis acid catalyzed ene-reactions. Preferred solvents may include benzene, toluene, xylene, hexane, chlorobenzene, methylene chloride, chloroform, dichloromethane, and dichloroethane.

Temperature

The reaction conditions employed in the process depend upon the nature, i.e. boiling point or stability, of the solvent and reactants or products. Reaction temperatures are generally in the range —30 degrees Celsius to 60 degrees Celsius, more preferably in the range between 0 and 40 degree Celsius. The process may be effected at any suitable pressure, e.g. atmospheric, superatmospheric or reduced pressure; although where the polyisobutene, enophile, or the reaction product is volatile or gaseous at the reaction temperature, the reaction pressure should be sufficient to maintain them in the liquid state e.g. in solution. Typically, the reaction is carried out at ambient pressure or at the autogenous pressure of the reactants at the respective reaction temperature. The process of the present invention may be effected batch-wise or continuously.

The starting materials and byproducts formed by the carbonyl-ene are readily removed by chromatographic or other means known in the art.

Fuel Compositions

The polyisobutenyl alcohols and substituted polyisobutenyl alcohols of formula I are suitable for use as additives in hydrocarbons fuels applications. The term "fuel" or "hydrocarbon fuel" refers to normally liquid hydrocarbons having boiling points in the range of gasoline fuels and/or diesel range. These compounds may by themselves assist in preventing and controlling deposits and are particularly suited for use as carrier fluids with other known nitrogen containing detergent additives. It is believed that these compounds will have improved compatibility with the detergent additives and act as a carrier to assist in removing and retarding deposits.

The carrier may also exhibit synergistc deposit control properties when used in combination with one or more nitrogen containing detergent additives. As carrier fluid, the polyisobutenyl alcohols and substituted polyisobutenyl alcohols of formula I are typically employed in the fuel in amounts ranging from about 100 to about 5000 parts per million (ppm) by weight of the hydrocarbon fuel, preferably from 400 to 3000 ppm of the fuel. Preferably the ratio of polyisobutenyl alcohols and substituted polyisobutenyl alcohols of formula I to the nitrogen containing detergent additive will range from about 0.5:1 to about 10:1, more preferably from 1:1 to 4:1 and more preferably about 2:1. In another aspect, the polyisobutenyl alcohols and substituted polyisobutenyl alcohols of formula I can be added in a large amount with the nitrogen containing detergent to form a fuel concentrate. When employed in a fuel concentrate, carrier fluid will generally be employed in amounts ranging from about 20 to about 60 weight percent, preferably form about 30 to about 50 weight percent. The fuel concentrate will contain approximately about 10 to 70 weight percent, preferably 10 to 50 weight percent and more preferably 20 to 40 weight percent of a nitrogen containing detergent.

Nitrogen Containing Detergent

The fuel compositions comprise a major amount of hydrocarbons boiling in the gasoline or diesel range, the polyisobutenyl alcohols and substituted polyisobutenyl alcohols of formula I, and will also contain at least one nitrogen-containing detergent additive. The proper concentration of detergent additive necessary to achieve the desired deposit control varies depending upon the type of fuel employed, the type of engine, and the presence of other additives. In general, the concentration of nitrogen containing detergent additive in hydrocarbon fuel will range from 50 to about 2500 ppm by weight and preferably from 50 to 1000 ppm by weight.

Suitable detergent additives for use in this invention include, for example, aliphatic hydrocarbyl amines, hydrocarbyl-substituted poly(oxyalkylene)amines, hydrocarbyl-substituted succinimides, Mannich reaction products, nitro and amino aromatic esters of polyalkylphenoxyalkanols, polyalkylphenoxyaminoalkanes, and mixtures thereof. The aliphatic hydrocarbyl-substituted amines which may be employed in the present invention are typically straight or branched chain hydrocarbyl-substituted amines having at least one basic nitrogen atom and wherein the hydrocarbyl group has a number average molecular weight of about 700 to 3,000. Preferred aliphatic hydrocarbyl-substituted amines include polyisobutenyl and polyisobutyl monoamines and polyamines. The aliphatic hydrocarbyl amines employed in this invention are prepared by conventional procedures known in the art. Such aliphatic hydrocarbyl amines and their preparations are described in detail in U.S. Pat. Nos. 3,438,757; 3,565,804; 3,574,576; 3,848,056; 3,960,515; 4,832,702; and 6,203,584, the disclosures of which are incorporated herein by reference.

Another class of detergent additives suitable for use in the present invention are the hydrocarbyl-substituted poly(oxyalkylene)amines, also referred to as polyether amines Typical hydrocarbyl-substituted poly(oxyalkylene)amines include hydrocarbyl poly(oxyalkylene)monoamines and polyamines wherein the hydrocarbyl group contains from 1 to about 30 carbon atoms, the number of oxyalkylene units will range from about 5 to 100, and the amine moiety is derived from ammonia, a primary alkyl or secondary dialkyl monoamine, or a polyamine having a terminal amino nitrogen atom. Preferably, the oxyalkylene moiety will be oxypropylene or oxybutylene or a mixture thereof. Such hydrocarbyl-substituted poly(oxyalkylene)amines are described, for example, in U.S.

Pat. No. 6,217,624 to Morris et al., and U.S. Pat. No. 5,112,364 to Rath et al., the disclosures of which are incorporated herein by reference. A preferred type of hydrocarbyl-substituted poly(oxyalkylene)monoamine is an alkylphenyl poly(oxyalkylene)monoamine wherein the poly(oxyalkylene) moiety contains oxypropylene units or oxybutylene units or mixtures of oxypropylene and oxybutylene units. Preferably, the alkyl group on the alkylphenyl moiety is a straight or branched-chain alkyl of 1 to 24 carbon atoms. An especially preferred alkylphenyl moiety is tetrapropenylphenyl, that is, where the alkyl group is a branched-chain alkyl of 12 carbon atoms derived from propylene tetramer.

An additional type of hydrocarbyl-substituted poly(oxyalkylene)amine finding use in the present invention are hydrocarbyl-substituted poly(oxyalkylene)aminocarbamates disclosed for example, in U.S. Pat. Nos. 4,288,612; 4,236,020; 4,160,648; 4,191,537; 4,270,930; 4,233,168; 4,197,409; 4,243,798 and 4,881,945, the disclosure of each of which are incorporated herein by reference. These hydrocarbyl poly(oxyalkylene)aminocarbamates contain at least one basic nitrogen atom and have an average molecular weight of about 500 to 10,000, preferably about 500 to 5,000, and more preferably about 1,000 to 3,000. A preferred aminocarbamate is alkylphenyl poly(oxybutylene)aminocarbamate wherein the amine moiety is derived from ethylene diamine or diethylene triamine.

A further class of detergent additives suitable for use in the present invention are the hydrocarbyl-substituted succinimides. Typical hydrocarbyl-substituted succinimides include polyalkyl and polyalkenyl succinimides wherein the polyalkyl or polyalkenyl group has an average molecular weight of about 500 to 5,000, and preferably about 700 to 3,000. The hydrocarbyl-substituted succinimides are typically prepared by reacting a hydrocarbyl-substituted succinic anhydride with an amine or polyamine having at least one reactive hydrogen bonded to an amine nitrogen atom. Preferred hydrocarbyl-substituted succinimides include polyisobutenyl and polyisobutanyl succinimides, and derivatives thereof. The hydrocarbyl-substituted succinimides finding use in the present invention are described, for example, in U.S. Pat. Nos. 5,393,309; 5,588,973; 5,620,486; 5,916,825; 5,954,843; 5,993,497; and 6,114,542, and British Patent No. 1,486,144, the disclosure of each of which are incorporated herein by reference.

Yet another class of detergent additives which may be employed in the present invention are Mannich reaction products which are typically obtained from the Mannich condensation of a high molecular weight alkyl-substituted hydroxyaromatic compound, an amine containing at least one reactive hydrogen, and an aldehyde. The high molecular weight alkyl-substituted hydroxyaromatic compounds are preferably polyalkylphenols, such as polypropylphenol and polybutylphenol, especially polyisobutylphenol, wherein the polyakyl group has an average molecular weight of about 600 to 3,000. The amine reactant is typically a polyamine, such as alkylene polyamines, especially ethylene or polyethylene polyamines, for example, ethylene diamine, diethylene triamine, triethylene tetramine, and the like. The aldehyde reactant is generally an aliphatic aldehyde, such as formaldehyde, including paraformaldehyde and formalin, and acetaldehyde. A preferred Mannich reaction product is obtained by condensing a polyisobutylphenol with formaldehyde and diethylene triamine, wherein the polyisobutyl group has an average molecular weight of about 1,000. The Mannich reaction products suitable for use in the present invention are described, for example, in U.S. Pat. Nos. 4,231,759 and 5,697,988, the disclosures of each of which are incorporated herein by reference.

A still further class of detergent additive suitable for use in the present invention are polyalkylphenoxyaminoalkanes. Preferred polyalkylphenoxyaminoalkanes include those having the formula:

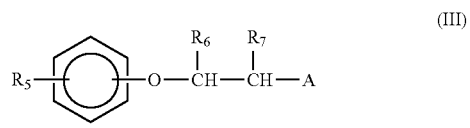

(III)

wherein: $R_5$ is a polyalkyl group having an average molecular weight in the range of about 600 to 5,000; $R_6$ and $R_7$ are independently hydrogen or lower alkyl having 1 to 6 carbon atoms; and A is amino, N-alkyl amino having about 1 to about 20 carbon atoms in the alkyl group, N,N-dialkyl amino having about 1 to about 20 carbon atoms in each alkyl group, or a polyamine moiety having about 2 to about 12 amine nitrogen atoms and about 2 to about 40 carbon atoms. The polyalkylphenoxyaminoalkanes of Formula III above and their preparations are described in detail in U.S. Pat. No. 5,669,939, the disclosure of which is incorporated herein by reference.

Mixtures of polyalkylphenoxyaminoalkanes and poly(oxyalkylene)amines are also suitable for use in the present invention. These mixtures are described in detail in U.S. Pat. No. 5,851,242, the disclosure of which is incorporated herein by reference.

A preferred class of detergent additive finding use in the present invention are nitro and amino aromatic esters of polyalkylphenoxyalkanols. Preferred nitro and amino aromatic esters of polyalkylphenoxyalkanols include those having the formula:

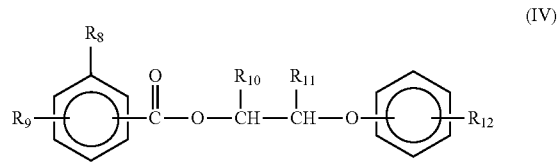

(IV)

wherein: $R_8$ is nitro or —$(CH_2)$—$NR_{13}R_{14}$, wherein $R_{13}$ and $R_{14}$ are independently hydrogen or lower alkyl having 1 to 6 carbon atoms and n is 0 or 1; $R_9$ is hydrogen, hydroxy, nitro or —$NR_{15}R_{16}$, wherein $R_{15}$ and $R_{16}$ are independently hydrogen or lower alkyl having 1 to 6 carbon atoms; $R_{10}$ and $R_{11}$ are independently hydrogen or lower alkyl having 1 to 6 carbon atoms; and $R_{12}$ is a polyalkyl group having an average molecular weight in the range of about 450 to 5,000. The aromatic esters of polyalkylphenoxyalkanols shown in Formula IV above and their preparations are described in detail in U.S. Pat. No. 5,618,320, the disclosure of which is incorporated herein by reference.

Mixtures of nitro and amino aromatic esters of polyalkylphenoxyalkanols and hydrocarbyl-substituted poly(oxyalkylene)amines are also preferably contemplated for use in the present invention. These mixtures are described in detail in U.S. Pat. No. 5,749,929, the disclosure of which is incorporated herein by reference. Preferred hydrocarbyl-substituted poly(oxyalkylene)amines which may be employed as detergent additives in the present invention include those having the formula:

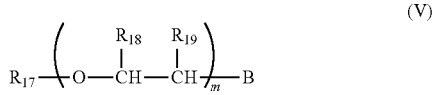

wherein: $R_{17}$ is a hydrocarbyl group having from about 1 to about 30 carbon atoms; $R_{18}$ and $R_{19}$ are each independently hydrogen or lower alkyl having about 1 to about 6 carbon atoms and each $R_{18}$ and $R_{19}$ is independently selected in each —O—$CHR_{18}$—$CHR_{19}$— unit; B is amino, N-alkyl amino having about 1 to about 20 carbon atoms in the alkyl group, N,N-dialkyl amino having about 1 to about 20 carbon atoms in each alkyl group, or a polyamine moiety having about 2 to about 12 amine nitrogen atoms and about 2 to about 40 carbon atoms; and m is an integer from about 5 to about 100. The hydrocarbyl-substituted poly(oxyalkylene)amines of Formula V above and their preparations are described in detail in U.S. Pat. No. 6,217,624, the disclosure of which is incorporated herein by reference. The hydrocarbyl-substituted poly (oxyalkylene)amines of Formula V are preferably utilized either by themselves or in combination with other detergent additives, particularly with the polyalkylphenoxyaminoalkanes of Formula III or the nitro and amino aromatic esters of polyalkylphenoxyalkanols shown in Formula IV. More preferably, the detergent additives employed in the present invention will be combinations of the hydrocarbyl-substituted poly (oxyalkylene)amines of Formula V with the nitro and amino aromatic esters of polyalkylphenoxyalkanols shown in Formula IV. A particularly preferred hydrocarbyl-substituted poly(oxyalkylene)amine detergent additive is dodecylphenoxy poly(oxybutylene)amine and a particularly preferred combination of detergent additives is the combination of dodecylphenoxy poly(oxybutylene)amine and 4-polyisobutylphenoxyethyl para-aminobenzoate.

Another type of detergent additive suitable for use in the present invention are the nitrogen-containing carburetor/injector detergents. The carburetor/injector detergent additives are typically relatively low molecular weight compounds having a number average molecular weight of about 100 to about 600 and possessing at least one polar moiety and at least one non-polar moiety. The non-polar moiety is typically a linear or branched-chain alkyl or alkenyl group having about 6 to about 40 carbon atoms. The polar moiety is typically nitrogen-containing. Typical nitrogen-containing polar moieties include amines (for example, as described in U.S. Pat. No. 5,139,534 and PCT International Publication No. WO 90/10051), ether amines (for example, as described in U.S. Pat. No. 3,849,083 and PCT International Publication No. WO 90/10051), amides, polyamides and amide-esters (for example, as described in U.S. Pat. Nos. 2,622,018; 4,729,769; and 5,139,534; and European Patent Publication No. 149, 486), imidazolines (for example, as described in U.S. Pat. No. 4,518,782), amine oxides (for example, as described in U.S. Pat. Nos. 4,810,263 and 4,836,829), hydroxyamines (for example, as described in U.S. Pat. No. 4,409,000), and succinimides (for example, as described in U.S. Pat. No. 4,292, 046).

In gasoline fuels, other fuel additives may be employed with the additive composition employed in the present invention, including, for example, oxygenates, such as t-butyl methyl ether, antiknock agents, such as methylcyclopentadienyl manganese tricarbonyl, and other dispersants/detergents, such as hydrocarbyl amines, or succinimides. Additionally, antioxidants, metal deactivators, demulsifiers and carburetor or fuel injector detergents may be present. In diesel fuel, other well known additives can be employed such as pour point depressants, flow improvers, certain improvers, and the like.

The gasoline fuels employed with the additive composition used in the present invention also include clean burning gasoline where levels of sulfur, aromatics and olefins range from typical amounts to only trace amounts.

A fuel-soluble, nonvolatile fluid or oil may also be used with the fuel additive composition employed in the present invention. The fluid is a chemically inert hydrocarbon-soluble liquid vehicle which substantially increases the nonvolatile residue (NVR), or solvent-free liquid fraction of the fuel additive composition while not overwhelmingly contributing to octane requirement increase. The fluid may be a natural or synthetic fluid, such as mineral oil, refined petroleum oils, synthetic polyalkanes and alkenes, including hydrogenated and unhydrogenated polyalphaolefins, and synthetic polyoxyalkylene-derived fluids, such as those described, for example, in U.S. Pat. No. 4,191,537 to Lewis, and polyesters, such as those described, for example, in U.S. Pat. No. 3,756, 793 to Robinson and U.S. Pat. No. 5,004,478 to Vogel et al., and in European Patent Application Nos. 356,726, published Mar. 7, 1990, and 382,159, published Aug. 16, 1990.

EXAMPLES

The following examples are presented to illustrate specific embodiments and synthetic preparations; and should not be interpreted as limitations on the scope.

Example 1

Preparation of ω-Hydroxymethylpolyisobutylene with Dimethylaluminum Chloride

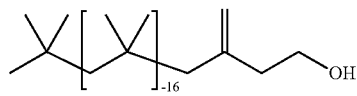

To a flask equipped with a magnetic stirrer and nitrogen inlet was added 5 grams of polyisobutylene (molecular weight 1000, 80% methylvinylidene), 136.5 milligrams of paraformaldehyde and 15 milliliters of anhydrous methylene chloride. Dimethylaluminum chloride (6.8 milliliters of a 1M solution in hexanes) was added via syringe in one portion. The reaction solution was then stirred for 16 hours at room temperature. The reaction was cooled in an ice bath and 15 milliliters of a 1% hydrochloric acid solution was added drop-wise. The resulting biphasic solution was extracted (3×15 milliliters) with hexanes. The combined organic layers were dried over magnesium sulfate, filtered and the solvent removed under vacuum to yield the crude product. The crude reaction product was purified by chromatography on silica gel eluting with hexane, followed by 10% ethyl acetate in hexane to yield 3.85 grams of the desired product as colorless oil. $^1$H-NMR (CDCl$_3$) δ: 4.95 (d, 1H), 4.85(d, 1H), 3.70 (t, 2H), 2.35(t, 2H), 2.00(s, 2H), 0.90-1.50(m, 137H).

Example 2

Preparation of
ω-4-Nitrophenylhydroxymethylpolyisobutylene with
Dimethylaluminum Chloride

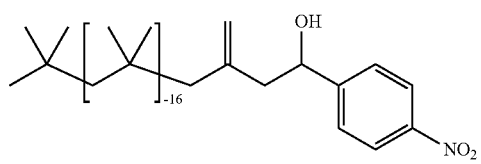

To a flask equipped with a magnetic stirrer and nitrogen inlet was added 5.35 grams of polyisobutylene (molecular weight 1000, 80% methylvinylidene), 0.74 grams of 4-nitrobenzaldehyde and 15 milliliters of anhydrous methylene chloride. Dimethylaluminum chloride (6.8 milliliters of a 1M solution in hexanes) was added via syringe in one portion. The reaction solution was then stirred for 16 hours at room temperature. The reaction was cooled in an ice bath and 15 milliliters of a 1% hydrochloric acid solution was added drop-wise. The resulting biphasic solution was extracted (3×15 milliliters) with hexanes. The combined organic layers were dried over magnesium sulfate, filtered and the solvent removed under vacuum to yield the crude product. The crude reaction product was purified by chromatography on silica gel eluting with hexane, followed by 10% ethyl acetate in hexane to yield 4.3 grams of the desired product as brown oil. $^1$H-NMR δ: 8.20(d, 2H), 7.55(d, 2H), 5.05(d, 1H), 5.00(d, 1H), 4.85(dd, 1H), 2.50(d, 2H), 2.05(s, 2H), 0.80-1.50(m, 137H).

Example 3

Preparation of ω-Hydroxymethylpolyisobutylene
with Boron Trifluoride Etherate

To a flask equipped with a magnetic stirrer and nitrogen inlet was added 20 grams of polyisobutylene (molecular weight 1000, 80% methylvinylidene), 0.6 grams of paraformaldehyde and 60 milliliters of anhydrous methylene chloride. Boron trifluoride etherate (0.123 milliliters) was added via syringe in one portion. The reaction mixture was stirred for 16 hours at room temperature. The mixture was diluted with 40 milliliters of methylene chloride followed by 2 milliliters of a saturated aqueous ammonium hydroxide solution. A precipitate was filtered out. The solution was washed with saturated sodium bicarbonate followed by saturated sodium chloride solution. The methylene chloride layer was dried with anhydrous magnesium sulfate. The solvent was removed under vacuum to yield the crude product. The crude reaction product was purified by chromatography on silica gel eluting with hexane, followed by 10% ethyl acetate in hexane solution to yield 6.85 grams of the desired product.

Example 4

Preparation of ω-Hydroxymethylpolyisobutylene
with Boron Trifluoride Etherate

To a flask equipped with a magnetic stirrer and nitrogen inlet was added 100 grams of polyisobutylene (molecular weight 1000, 80% methylvinylidene), 0.6 grams of paraformaldehyde and 60 milliliters of anhydrous methylene chloride. Boron trifluoride etherate (0.123 milliliters) was added via syringe in one portion. The reaction mixture was stirred for 16 hours at room temperature. The mixture was diluted with 40 milliliters of methylene chloride followed by 2 milliliters of a saturated aqueous ammonium hydroxide solution. A precipitate was filtered out. The solution was washed with saturated sodium bicarbonate followed by saturated sodium chloride solution. The methylene chloride layer was dried with anhydrous magnesium sulfate. The solvent was removed under vacuum to yield the crude product. The crude reaction product was purified by chromatography on silica gel eluting with hexane, followed by 10% ethyl acetate in hexane solution to yield 13.6 grams of the desired product.

Example 5

Preparation of
ω-4-Nitrophenylhydroxymethylpolyisobutylene with
Boron Trifluoride Etherate To a flask equipped with a magnetic stirrer and nitrogen inlet was added 100 grams of polyisobutylene (molecular weight 1000, 80% methylvinylidene), 3.02 grams of 4-nitrobenzaldehyde and 60 milliliters of anhydrous methylene chloride. Boron trifluoride etherate (0.123 milliliters) was added via syringe in one portion. The reaction mixture was stirred for 16 hours at room temperature. The mixture was diluted with 40 milliliters of methylene chloride followed by 2 milliliters of a saturated aqueous ammonium hydroxide solution. A precipitate was filtered out. The solution was washed with saturated sodium bicarbonate followed by saturated sodium chloride solution. The methylene chloride layer was dried with anhydrous magnesium sulfate. The solvent was removed under vacuum to yield the crude product. The crude reaction product was purified by chromatography on silica gel eluting with hexane, followed by 10% ethyl acetate in hexane solution to yield 15.2 grams of the desired product.

Example 6

Preparation of ω-Hydroxymethylpolyisobutylene
with Methyltrichlorosilane

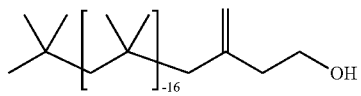

To a flask equipped with a magnetic stirrer and nitrogen inlet was added 5.35 grams of polyisobutylene (molecular weight 1000, 80% methylvinylidene), 146 milligrams of paraformaldehyde and 15 milliliters of anhydrous methylene chloride. Methyltrichlorosilane (0.86 milliliters) was added via syringe in one portion. The reaction mixture was stirred for 16 hours at room temperature. The reaction was cooled in an ice bath and 15 milliliters of a 0.5N hydrochloric acid solution was added drop-wise. The addition of the acids caused a silicon based gel to form. The methylene chloride/HCl(aq) solution was decanted from the gel and the gel is washed (3×) with a 10% ethyl acetate in hexane solution. The aqueous layer was extracted with hexanes (3×). All of the organic layers were combined, dried over magnesium sulfate, filtered and the solvent removed under vacuum to yield the crude product. The crude reaction product was purified by chromatography on silica gel eluting with hexane, followed by 10% ethyl acetate in hexane to yield 3.85 grams of the desired product as colorless oil. $^1$H-NMR (CDCl$_3$) δ: 4.95 (d, 1H), 4.85(d, 1H), 3.70 (t, 2H), 2.35 (t, 2H), 2.00 (s, 2H), 0.90-1.50 (m, 137H).

Example 7

Preparation of ω-Hydroxymethylpolyisobutylene with Dimethyldichlorosilane

To a flask equipped with a magnetic stirrer and nitrogen inlet was added 5.06 grams of polyisobutylene (molecular weight 1000, 80% methylvinylidene), 138 milligrams of paraformaldehyde and 15 milliliters of anhydrous methylene chloride. Dimethyldichlorosilane (0.83 milliliters) was added via syringe in one portion. The reaction mixture was stirred for 16 hours at room temperature. The reaction was cooled in an ice bath and 15 milliliters of a 0.5N hydrochloric acid solution was added drop-wise. The resulting biphasic solution was extracted with hexanes (3×15 milliliters). The combined organic layers were dried over magnesium sulfate, filtered and the solvent removed under vacuum to yield the crude product. The crude reaction product was purified by chromatography on silica gel eluting with hexane, followed by 10% ethyl acetate in hexane to yield 3.0 grams of the desired product.

Example 8

Preparation of ω-Hydroxymethylpolyisobutylene with Methyltrichlorosilane

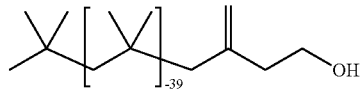

To a flask equipped with a magnetic stirrer and nitrogen inlet was added 7.26 grams of polyisobutylene (molecular weight 2300, 80% methylvinylidene), 86 milligrams of paraformaldehyde and 15 milliliters of anhydrous methylene chloride. Methyltrichlorosilane (0.51 milliliters) was added via syringe in one portion. The reaction mixture was stirred for 16 hours at room temperature. The reaction was cooled in an ice bath and 15 milliliters of a 0.5N hydrochloric acid solution was added drop-wise. The addition of the acids caused a silicon based gel to form. The methylene chloride/HCl(aq) solution was decanted from the gel and the gel is washed (3×) with a 10% ethyl acetate in hexane solution. The combined organic layers were separated and the aqueous layer extracted (3×) with hexanes. All of the organic layers were combined, dried with magnesium sulfate and the solvent removed under vacuum to yield the crude product. The reaction yielded 2.32 grams of the desired product as colorless oil. $^1$H-NMR (CDCl$_3$) δ: 4.95 (d, 1H), 4.85(d, 1H), 3.70 (t, 2H), 2.35 (t, 2H), 2.00 (s, 2H), 0.90-1.50 (m, 321H).

Example 9

Preparation of ω-Hydroxymethylpolyisobutylene with Phenyltrichlorosilane

To a flask equipped with a magnetic stirrer and nitrogen inlet was added 5.16 grams of polyisobutylene (molecular weight 1000, 80% methylvinylidene), 141 milligrams of paraformaldehyde and 15 milliliters of anhydrous methylene chloride. Phenyltrichlorosilane (1.1 milliliters) was added via syringe in one portion. The reaction mixture was stirred for 16 hours at room temperature. The reaction was cooled in an ice bath and 15 milliliters of a 0.5N hydrochloric acid solution was added drop-wise. The resulting biphasic solution was extracted with hexanes (3×15 milliliters). The combined organic layers were dried over magnesium sulfate, filtered and the solvent removed under vacuum to yield the crude product. The reaction yielded 2.1 grams of the desired product.

Example 10

Preparation of ω-Hydroxymethylpolyisobutylene with Methyltrichlorosilane

To a flask equipped with a magnetic stirrer and nitrogen inlet was added 5.53 grams of polyisobutylene (molecular weight 1000, 80% methylvinylidene), 151 milligrams of paraformaldehyde and 15 milliliters of anhydrous methylene chloride. Methyltrichlorosilane (2.96 milliliters) was added via syringe in one portion. The reaction mixture was stirred for 16 hours at room temperature. The reaction was cooled in an ice bath and 15 milliliters of a 0.5N hydrochloric acid solution was added drop-wise. The addition of the acids caused a silicon based gel to form. The methylene chloride/HCl(aq) solution was decanted from the gel and the gel is washed (3×) with a 10% ethyl acetate in hexane solution. The combined organic layers were separated and the aqueous layer extracted (3×) with hexanes. All of the organic layers were combined, dried with magnesium sulfate and the solvent removed under vacuum to yield the crude product. The reaction yielded 3.8 grams of the desired product as colorless oil.

Example 11

Preparation of ω-Hydroxymethylpolyisobutylene with Methyltrichlorosilane

To a flask equipped with a magnetic stirrer and nitrogen inlet was added 5.14 grams of polyisobutylene (molecular weight 1000, 80% methylvinylidene), 140 milligrams of paraformaldehyde and 15 milliliters of anhydrous methylene chloride. Methyltrichlorosilane (0.66 milliliters) was added via syringe in one portion. The reaction mixture was stirred for 16 hours at room temperature. The reaction was cooled in an ice bath and 15 milliliters of a 0.5N hydrochloric acid solution was added drop-wise. The addition of the acids caused a silicon based gel to form. The methylene chloride/HCl(aq) solution was decanted from the gel and the gel is washed (3×) with a 10% ethyl acetate in hexane solution. The combined organic layers were separated and the aqueous layer extracted (3×) with hexanes. All of the organic layers were combined, dried with magnesium sulfate and the solvent removed under vacuum to yield the crude product. The reaction yielded 3.28 grams of the desired product as colorless oil.

What is claimed is:

1. A compound of the formula:

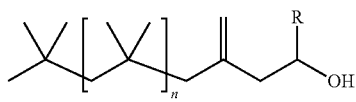

wherein n is an integer from 5 to 90, R is selected from the group consisting of hydrogen, haloalkyl, alkoxycarbonyl and substituted aryl wherein at least one substituent group of the substituted aryl is selected from cyano, nitro and alkoxycarbonyl.

2. The compound of claim 1 wherein n is an integer from 6 to 52.

3. The compound of claim 2 wherein n is an integer from 14 to 42.

4. The compound of claim 1 wherein R is selected from hydrogen, alkoxycarbonyl and a mono substituted aryl.

5. The compound of claim 1, wherein R is hydrogen.

6. The compound of claim 1, wherein R is an alkoxycarbonyl group of the formula —C(O)OR$_2$ wherein R$_2$ is alkyl from 1 to 6 carbon atoms.

7. The compound of claim 1, wherein R is a substituted aryl group.

8. The compound of claim 1, wherein the compound is of the formula II

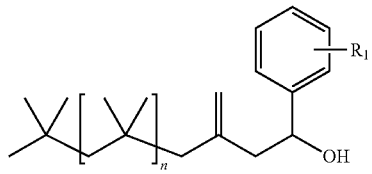

wherein R$_1$ is selected from the group consisting of cyano, nitro and —C(O)OR$_2$ wherein R$_2$ is alkyl from 1 to 6 carbon atoms.

9. The compound of claim 8 wherein R$_1$ is in the para position.

10. The compound of claim 9 wherein R$_1$ is selected from the group of cyano and nitro.

11. The compound of claim 9 wherein R$_1$ is —C(O)OR$_2$ wherein R$_2$ is alkyl from 1 to 6 carbon atoms.

12. A fuel composition comprising a major amount of hydrocarbons boiling in the gasoline or diesel range;

a. 100 to 5000 ppm of the compound:

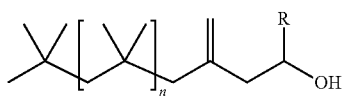

wherein n is an integer from 5 to 90, R is selected from the group consisting of hydrogen, alkoxycarbonyl and substituted aryl wherein at least one substituent group of the substituted aryl is selected from cyano, nitro and alkoxycarbonyl; and b. 50 to 2500 ppm of a nitrogen containing detergent.

13. The fuel composition of claim 12 wherein the nitrogen containing detergent is selected from the group consisting of aliphatic hydrocarbyl amines, hydrocarbyl-substituted poly(oxyalkylene)amines, hydrocarbyl-substituted succinimides, Mannich reaction products, nitro and amino aromatic esters of polyalkylphenoxyalkanols, polyalkylphenoxyaminoalkanes, and mixtures thereof.

* * * * *